(12) United States Patent
Kang et al.

(10) Patent No.: US 9,598,705 B2
(45) Date of Patent: Mar. 21, 2017

(54) THERMOCOCCUS ONNURINEUS MC02 AND METHOD OF HYDROGEN PRODUCTION USING THEREOF

(71) Applicant: Korea Institute of Ocean Science & Technology, Gyeonggi-Do (KR)

(72) Inventors: Sung Gyun Kang, Gyeonggi-do (KR); Jung Hyun Lee, Gyeonggi-do (KR); Hyun Sook Lee, Gyeonggi-do (KR); Kae Kyoung Kwon, Gyeonggi-do (KR); Tae Wan Kim, Gyeonggi-do (KR); Yun Jae Kim, Gyeonggi-do (KR); Min Sik Kim, Gyeonggi-do (KR); Seong Hyuk Lee, Gyeonggi-do (KR); Seung Seob Bae, Gyeonggi-do (KR); Ae Ran Choi, Gyeonggi-do (KR)

(73) Assignee: KOREA INSTITUTE OF OCEAN SCIENCE & TECHNOLOGY, Gyeonggi-Do (KR)

( * ) Notice: Subject to any disclaimer, the term of this patent is extended or adjusted under 35 U.S.C. 154(b) by 101 days.

(21) Appl. No.: 14/480,332

(22) Filed: Sep. 8, 2014

(65) Prior Publication Data

US 2015/0132819 A1    May 14, 2015

(30) Foreign Application Priority Data

Nov. 13, 2013    (KR) .................. 10-2013-0137344

(51) Int. Cl.
| | | |
|---|---|---|
| *C12N 1/21* | (2006.01) | |
| *C12P 3/00* | (2006.01) | |
| *C12N 15/67* | (2006.01) | |
| *C12N 1/20* | (2006.01) | |
| *C07K 14/195* | (2006.01) | |

(52) U.S. Cl.
CPC .............. *C12P 3/00* (2013.01); *C07K 14/195* (2013.01); *C12N 1/20* (2013.01); *C12N 15/67* (2013.01)

(58) Field of Classification Search
None
See application file for complete search history.

(56) References Cited

FOREIGN PATENT DOCUMENTS

| KR | 10-2011-0094092 A | 8/2011 |
|---|---|---|
| KR | 10-2012-0103238 A | 9/2012 |

OTHER PUBLICATIONS

M.Kim et al. "CO-Dependent H2 Production by Genetically Engineered Thermococcus onnurineus NA1", Applied and Environmental Microbiology 79(6):2048-2053 and supplementary material (Jan. 2013).*
H.S. Lee et al. "The Complete Genome Sequence of Thermococcus onnurineus NA1 Reveals a Mixed Heterotrophic and Carboxydotrophic Metabolism", J. Bacterilogy 190(22):7491-7499 (Nov. 2008).*
Bae SS et al. H2 production from CO, formate or starch using the hyperthermophilic archaeon, Thermococcus onnurineus, Biotechnol Lett. Jan. 2012; 34(1):75-79.
Moon YJ et al., Proteome analyses of hydrogen-producing hyperthermophilic archaeon Thermococcus onnurineus NA1 in different one-carbon substrate culture conditions, Mol Cell Proteomics. Jun. 2012;11(6):M111.015420.

* cited by examiner

*Primary Examiner* — Rebecca Prouty
(74) *Attorney, Agent, or Firm* — The PL Law Group, PLLC (57) ABSTRACT

The present invention provides *Thermococcus onnurineus* MC02 strain (accession no. KCTC12511BP) having increased hydrogen production ability, wherein the expression of rchA gene of the strain increases. Also, the present invention provides a method for producing the strain belonged to the genus *Thermococcus* having increased hydrogen production ability comprising, increasing the expression of rchA gene of the strain, and hydrogen production method using the strain.

5 Claims, 8 Drawing Sheets

```
                       SEQUENCE LISTING

<160> NUMBER OF SEQ ID NOS: 6

<210> SEQ ID NO 1
<211> LENGTH: 367
<212> TYPE: PRT
<213> ORGANISM: Thermococcus onnurineus NA1

<400> SEQUENCE: 1

Met Gly Val Ile Val Val Gln Pro Ser Gly Arg Cys Asp Ala Thr Cys
1               5                   10                  15

Ala Asn Cys Ile Trp Arg Glu Arg Leu Ser Gly Val Met Leu Pro Gly
                20                  25                  30

Asp Val Leu Pro Arg Ile Ala Ser Leu Leu Asp Gly Phe Arg Phe Asp
            35                  40                  45

Glu Gly Ile Leu Met Cys Pro Asn Pro Phe Leu His Pro Lys Ile Lys
        50                  55                  60

Ile Ile Tyr Asp Glu Leu Arg Asp Ile Ser Lys Arg Val Thr Val Phe
65                  70                  75                  80

Ile Pro Leu Thr Ala Ser Leu Ser Asn Leu Arg Val Asp Val Leu Ala
                85                  90                  95

Asp Val Asp Met Ile Ser Ile Ile Val Pro Pro Met Ile Asp Ile Lys
                100                 105                 110

Arg Gly Asp Thr Leu Ile Arg Ala Leu Glu Ser Arg Gly Ile Asp His
            115                 120                 125

Ile Glu Ala Tyr Leu Val Phe Asn Ser Ser Ser Asp Pro Gly Glu Ile
        130                 135                 140

Leu Arg Lys Ile Gly Glu Cys Met Lys Arg Gly Leu Arg Ile Thr Val
145                 150                 155                 160

Gly Pro Ser Leu Phe Ser Pro Pro Ser Gly Asp Met Phe Ile Glu Ser
                165                 170                 175

Ile Ser Ala Arg Lys Asp Val Glu Leu Gly Leu His Tyr Gly Arg Lys
                180                 185                 190

Tyr Leu Tyr Ser Ala Met Lys Val Phe Leu Asn Asp Tyr Pro Ile Thr
            195                 200                 205

Leu Leu Met Ser Pro Met Asp Pro Cys Arg His Leu Tyr Val Asn Pro
        210                 215                 220

Tyr Gly Ile Ile Ser Lys Cys Pro Asn Ser Asn Phe Ser Val Ser Tyr
225                 230                 235                 240

Arg Glu Met Thr Arg Glu Leu Leu Arg Lys Ile Phe Phe Ser Pro Cys
                245                 250                 255

Pro Asn Asn Lys Asn Pro Ser Phe Val Pro Lys Val Glu Ile Ser Phe
                260                 265                 270

Val Thr Ser Ser Gly Ile Lys Ile Pro Gly Asp Ile Met Glu Leu Leu
            275                 280                 285
```

```
Glu Leu Ile Ser Gln Thr Arg Ser Phe Arg Ala Ala Cys Lys Ile Met
    290                 295                 300

Gly Val Ser Pro Ser Thr Tyr Trp Glu Arg Ile Arg Asp Ile Glu Glu
305                 310                 315                 320

Lys Leu Gly Arg Arg Leu Ile Val Ser Val Lys Gly Gly Arg Lys Lys
                    325                 330                 335

Gly Ile Thr Val Leu Thr Gly Val Ala Leu Asp Leu Leu Lys Glu Tyr
                340                 345                 350

Gln Arg Ile Arg Glu Arg Val Leu Leu Ser Leu Asn Glu Arg Phe
            355                 360                 365

<210> SEQ ID NO 2
<211> LENGTH: 372
<212> TYPE: PRT
<213> ORGANISM: Candidatus Korarchaeum cryptofilum OPF8

<400> SEQUENCE: 2

Met Gly Leu Ile Ala Ser Arg Glu Val Glu Leu Ile Val Arg Ala Val
1               5                   10                  15

Gly Lys Cys Tyr Leu Ser Cys Pro His Cys Asn Trp Asn Glu Glu Ile
                20                  25                  30

Arg Glu Ala Tyr Leu Arg Glu Ser Leu Glu Leu Leu Asp Ile
            35                  40                  45

Leu Ile Gly Glu Gly Tyr Lys Pro Glu Val Tyr Phe Ser Cys Pro Asp
50                  55                  60

Pro Leu His Pro Ser Leu Ser Ser Leu Ile Ser Ala Pro Ile Glu
65                  70                  75                  80

Arg Gly Leu Lys Ser Thr Val Leu Val Pro Ala Arg Thr Arg Ser Asp
                85                  90                  95

Arg Lys Ala Trp Glu Ser Leu Leu Asn Ala Ser Arg Ile Phe Ile Phe
            100                 105                 110

Ser Ser Ser Ile Arg Asp Leu Arg Gly Ser Lys Glu Phe Leu Lys Phe
            115                 120                 125

Leu Ile Ser Asn Gly Ser Asp Leu Lys Leu Met Phe Leu Arg Gly Ser
130                 135                 140

Lys Asp Asp Leu Asn Gln Ile Leu Glu Phe Ala Arg Asp Met Gly Leu
145                 150                 155                 160

Glu Leu Trp Val Ala Pro Pro Leu Phe Arg Ile Pro Lys Val Glu Gly
                165                 170                 175

Leu Asp Glu Asn Leu Glu Leu Gly Lys Gln Val Ala Lys Phe Met Gly
            180                 185                 190

Ile Tyr Asp Val Arg Ile Ala Phe Lys Gly Asp Phe Pro Phe Lys Ile
        195                 200                 205

Ile Glu Gly Pro Arg Cys Glu Ile Gly Cys Lys Leu Leu Tyr Leu Asp
210                 215                 220

Pro Glu Gly Arg Leu Gly Arg Cys Pro Phe Asn Ala Met Asp Gln Leu
225                 230                 235                 240

Asn Ser Pro Pro Leu Glu Ala Ile Arg Ile Leu Asp Glu Ser Cys Glu
                245                 250                 255

Arg Gly Glu Gly Arg Lys Phe Glu Leu Val Pro Ser Ile Lys Leu Ile
            260                 265                 270

Thr Gly Asn Gly Glu Glu Ile Tyr Glu Arg Asp Leu Glu Leu Leu Ser
        275                 280                 285

Leu Ile Glu Glu Leu Gly Ser Leu Ser Gln Ala Ala Arg Thr Ile Gly
290                 295                 300
```

```
Ala Thr Pro Ser Ser Ile Phe Lys Arg Ile Arg Met Glu Gly Val
305                 310                 315                 320

Leu Gly Leu Arg Leu Ile Thr Ser Ser Arg Gly Gly Tyr Leu Arg Gly
            325                 330                 335

Gly Val Arg Leu Thr Pro Glu Cys Glu Gly Leu Val Arg Arg Tyr Arg
            340                 345                 350

Glu Leu Lys Val Ser Ile Ile Asn Arg Tyr Arg Leu Ser Leu Met Glu
            355                 360                 365

Lys Leu Asp Gly
            370

<210> SEQ ID NO 3
<211> LENGTH: 350
<212> TYPE: PRT
<213> ORGANISM: Thermococcus guaymasensis

<400> SEQUENCE: 3

Met Gly Met Thr Leu Leu Val Ile Gln Pro Ser Thr Lys Cys Asp Gly
1               5                   10                  15

Ser Cys Ile Ile Cys Pro Trp Arg Glu Lys Phe Gly Cys Thr Gly Met
            20                  25                  30

Met Leu Pro Pro Leu Ala Leu Asp Ala Leu Ala Glu Asn Leu Asn Gly
            35                  40                  45

Phe Arg Phe Asp Glu Cys Val Val Ile Cys Pro Asn Pro Phe Ser His
50                  55                  60

Pro Lys Ile Asp Val Ile Leu Asp Lys Thr Gln Glu Leu Cys Asp Arg
65                  70                  75                  80

Val Asp Val Phe Val Pro Ile Ser Gly Leu Lys Asn Val Ala Arg Ser
                85                  90                  95

Gly Gln Leu Lys Lys Ile Ser Asn Asn Ile His Ala Leu Ile Ile Leu
            100                 105                 110

Val Asn Ser Gln Lys Ala Met Thr Ser Ser Val Gln Thr Ile Lys Asn
            115                 120                 125

Leu Leu Ser Phe Gly Phe Asp Asn Ile Glu Ala Tyr Ile Pro Leu Gly
130                 135                 140

Leu Ser Phe Asp Phe Ala Glu Ile Leu Ser Leu Ile Gly Ile Cys Arg
145                 150                 155                 160

Arg Leu Gly Leu Arg Ile Thr Val Gly Pro Arg Phe Tyr Glu Lys Ala
                165                 170                 175

Pro Thr Glu Glu Phe Leu Lys Lys Leu Ala Lys Arg Glu Asn Thr Glu
            180                 185                 190

Val Gly Leu His Tyr Gly Val Lys Tyr Met Tyr His Ala Leu Lys Val
            195                 200                 205

Phe Phe Asp Tyr Pro Val Thr Leu Leu Thr Ser Pro Ser Pro Glu
210                 215                 220

Ser Cys Lys Thr Leu Tyr Val Asn Pro Tyr Gly Asn Val Ser Lys Cys
225                 230                 235                 240

Pro His Ser Lys Leu Ser Ile Ser Tyr Arg His Leu Ser Thr Glu Tyr
                245                 250                 255

Leu Arg Lys Ile Leu Phe Ser Pro Cys Pro Leu Ser Gln Asn Ala Val
            260                 265                 270

Gln Leu Thr Pro Lys Val Lys Val Ser Phe Val Thr Gln Glu Gly Val
            275                 280                 285

Glu Ile Pro Pro Asp Val Met Glu Leu Leu Glu Leu Ile Ser Gln Leu
290                 295                 300
```

```
Lys Ser Phe Arg Ala Ala Cys Lys Ala Met Gly Val Ser Pro Ser Thr
305                 310                 315                 320

Tyr Trp Glu Arg Ile Lys Glu Leu Glu Asp Lys Leu Gly Val Ser Ile
            325                 330                 335

Leu Ile Thr Val Arg Gly Gly Arg Lys Lys Gly Val Thr Ile
            340                 345                 350

<210> SEQ ID NO 4
<211> LENGTH: 375
<212> TYPE: PRT
<213> ORGANISM: Thermococcus sp. AM4

<400> SEQUENCE: 4

Met Gly Met Ser Leu Leu Val Ile Gln Pro Ser Thr Lys Cys Asp Gly
1               5                   10                  15

Gly Cys Leu Ile Cys Pro Trp Arg Glu Lys Phe Gly Cys Thr Gly Val
            20                  25                  30

Met Leu Pro Pro Glu Val Val Asp Ile Leu Ala Glu Asn Leu Asp Gly
            35                  40                  45

Phe Arg Phe Asp Glu Cys Val Ile Thr Cys Pro Asn Pro Phe Ser His
    50                  55                  60

Pro Lys Ile Asp Val Ile Val Asn Lys Thr Gln Glu Ile Cys Asp Arg
65                  70                  75                  80

Ile Asp Met Phe Ile Thr Ile Pro Gly Leu Lys Asn Val Ala Arg Ser
                85                  90                  95

Gly Gln Leu Lys Lys Ile Ser Asp Asn Val His Ala Leu Ile Ile Leu
            100                 105                 110

Val Asp Ser Gln Lys Ala Met Met Ser Ser Ile Gln Thr Ile Lys Asn
            115                 120                 125

Leu Leu Ser Phe Gly Val Asp Asn Ile Glu Ala Tyr Ile Pro Leu Gly
    130                 135                 140

Ser Ser Phe Asp Phe Ala Glu Ile Leu Ser Leu Ile Gly Ile Cys Arg
145                 150                 155                 160

Arg Leu Gly Leu Arg Ile Thr Val Gly Pro Arg Phe Tyr Glu Lys Ala
                165                 170                 175

Pro Thr Glu Glu Phe Leu Lys Lys Leu Ala Lys Arg Glu Asn Thr Glu
            180                 185                 190

Val Gly Leu His Tyr Gly Ile Lys Tyr Ile Tyr His Ala Leu Lys Val
            195                 200                 205

Phe Phe Asp Asp Tyr Pro Val Thr Leu Leu Thr Ser Pro Ser Ser Glu
    210                 215                 220

Asn Cys Lys Thr Ile Tyr Val Asn Pro Tyr Gly Asn Val Ser Lys Cys
225                 230                 235                 240

Pro His Ser Lys Leu Ser Ile Asn Tyr Arg His Ile Ser Thr Glu Tyr
                245                 250                 255

Leu Arg Lys Met Leu Phe Ser Pro Cys Pro Leu Ser Gln Asn Ala Leu
            260                 265                 270

Gln Leu Thr Pro Lys Val Lys Val Ser Phe Val Thr Arg Asp Gly Val
            275                 280                 285

Glu Ile Pro Ser Asp Ile Met Glu Leu Leu Glu Leu Ile Ser Gln Leu
    290                 295                 300

Lys Ser Phe Arg Ala Ala Cys Lys Ala Ile Gly Val Ser Pro Ser Thr
305                 310                 315                 320

Tyr Trp Glu Arg Ile Lys Glu Leu Glu Tyr Lys Leu Gly Met Ser Leu
                325                 330                 335
```

-continued

```
Leu Ile Thr Val Arg Gly Gly Arg Lys Lys Gly Ile Thr Val Leu Thr
            340                 345                 350

Gly Phe Ala Arg Asp Ile Leu Glu Glu Tyr Arg Arg Val Arg Glu Lys
        355                 360                 365

Val Leu Leu Ser Leu Tyr Thr
    370                 375

<210> SEQ ID NO 5
<211> LENGTH: 372
<212> TYPE: PRT
<213> ORGANISM: Thermococcus barophilus

<400> SEQUENCE: 5

Met Asp Met Ser Ile Leu Ala Val Gln Pro Ser Ser Lys Cys Asp Ser
1               5                   10                  15

Ser Cys Leu Ile Cys Pro Trp Lys Glu Lys Phe Gly Cys Ala Gly Ile
            20                  25                  30

Met Leu Pro Leu Glu Ala Leu Glu Ile Leu Ser Ser His Leu Glu Asp
        35                  40                  45

Phe Arg Phe Asp Glu Gly Leu Leu Thr Cys Pro Asn Pro Leu Leu His
    50                  55                  60

Pro Lys Ile Asp Ile Ile Leu Arg Gln Thr Met Glu Leu Cys Lys Lys
65                  70                  75                  80

Leu Thr Leu Phe Ile Pro Val Ser Val Ser Arg Asn Phe Leu Asn Lys
                85                  90                  95

Thr Ser Leu Glu Asn Val Asp Phe Ile Ser Leu Ile Ile Pro Ser Tyr
            100                 105                 110

Lys Asp Ile Lys Ser Asn Leu Gln Thr Val Lys Met Leu Leu Ser Gln
        115                 120                 125

Gly Ile Asp Asn Leu Glu Ala Tyr Ile Leu Leu Asp Ser Asn Ser Asp
    130                 135                 140

Phe Ala Glu Ile Leu Ser Thr Ile Glu Leu Cys Lys Ser Tyr Gly Leu
145                 150                 155                 160

Lys Ile Thr Leu Gly Pro Lys Leu Tyr Ala Ser Pro Tyr Ala Asp Lys
                165                 170                 175

Phe Leu Glu Lys Ile Ala Lys Lys Glu Asn Val Glu Ile Gly Leu His
            180                 185                 190

Tyr Gly Arg Lys Tyr Phe Tyr Asn Ala Ile Lys Val Phe Ile Asp Asn
        195                 200                 205

Tyr Pro Val Thr Leu Leu Thr Ser Pro Gly Ala Glu Asn Cys Lys Thr
    210                 215                 220

Leu Tyr Leu Asn Pro Tyr Gly Asn Phe Ser Lys Cys Pro Leu Ser Arg
225                 230                 235                 240

Phe Glu Val Asn Tyr Lys Lys Ile Thr Lys Asp Leu Arg Lys Met
                245                 250                 255

Leu Phe Ser Pro Cys Ala Ile Asn Arg Asn Val Val Gly Leu Ser Pro
            260                 265                 270

Lys Ile Arg Val Ser Phe Val Thr Lys Glu Gly Val Glu Ile Pro Gly
        275                 280                 285

Glu Ile Leu Glu Leu Leu Glu Leu Ile Ser Gln Val Asn Ser Phe Arg
    290                 295                 300

Ala Ala Cys Lys Ala Leu Gly Val Ser Pro Ser Thr Tyr Trp Glu Lys
305                 310                 315                 320

Ile Arg Ser Leu Glu Glu Lys Leu Gly Ile Ser Leu Ile Ile Ser Val
                325                 330                 335
```

-continued

```
Arg Gly Gly Arg Lys Lys Gly Ile Thr Ile Leu Thr Glu Phe Ala Lys
            340                 345                 350

Asp Leu Leu Lys Glu Tyr Arg Glu Ile Arg Glu Lys Ala Ile Val Ser
            355                 360                 365

Leu Tyr Glu Tyr
    370

<210> SEQ ID NO 6
<211> LENGTH: 324
<212> TYPE: PRT
<213> ORGANISM: Artificial Sequence
<220> FEATURE:
<223> OTHER INFORMATION: consensus of rchA gene

<400> SEQUENCE: 6

Met Met Ser Leu Leu Val Val Gln Pro Ser Thr Lys Cys Asp Gly Ser
1               5                   10                  15

Cys Leu Ile Cys Pro Trp Arg Glu Lys Phe Gly Cys Thr Gly Val Met
            20                  25                  30

Leu Pro Glu Val Leu Asp Ile Leu Ala Leu Asp Gly Phe Arg Phe Asp
        35                  40                  45

Glu Val Leu Thr Cys Pro Asn Pro Phe Leu His Pro Lys Ile Asp Ile
    50                  55                  60

Ile Leu Thr Glu Ile Cys Lys Arg Val Thr Val Phe Ile Pro Ile Ser
65                  70                  75                  80

Gly Lys Asn Arg Lys Ile Leu Asn Val Ile Ile Val Ser Lys Asp
                85                  90                  95

Ile Lys Ser Ser Ile Gln Thr Ile Lys Leu Leu Ser Gly Ile Asp Asn
            100                 105                 110

Ile Glu Ala Tyr Ile Leu Ser Ser Asp Phe Ala Glu Ile Leu Ser Leu
        115                 120                 125

Ile Gly Ile Cys Arg Arg Leu Gly Leu Arg Ile Thr Val Gly Pro Arg
    130                 135                 140

Leu Tyr Pro Glu Phe Leu Glu Lys Ile Ala Lys Arg Glu Asn Val Glu
145                 150                 155                 160

Val Gly Leu His Tyr Gly Lys Tyr Ile Tyr Ala Leu Lys Val Phe Asp
                165                 170                 175

Asp Tyr Pro Val Thr Leu Leu Thr Ser Pro Glu Cys Lys Thr Leu Tyr
            180                 185                 190

Val Asn Pro Tyr Gly Asn Val Ser Lys Cys Pro Ser Lys Ser Ile Tyr
        195                 200                 205

Arg Ile Ser Glu Leu Arg Lys Ile Leu Phe Ser Pro Cys Pro Leu Asn
    210                 215                 220

Val Leu Thr Pro Lys Val Lys Val Ser Phe Val Thr Glu Gly Val Glu
225                 230                 235                 240

Ile Pro Asp Ile Met Glu Leu Leu Glu Leu Ile Ser Gln Val Lys Ser
                245                 250                 255

Phe Arg Ala Ala Cys Lys Ala Ile Gly Val Ser Pro Ser Thr Tyr Trp
            260                 265                 270

Glu Arg Ile Arg Glu Leu Glu Glu Lys Leu Gly Ile Ser Leu Ile Ile
        275                 280                 285

Ser Val Arg Gly Gly Arg Lys Lys Gly Ile Thr Ile Leu Thr Gly Phe
    290                 295                 300
```

-continued

```
Ala Arg Asp Leu Leu Lys Glu Tyr Arg Arg Ile Arg Glu Lys Val Leu
305                 310                 315                 320

Leu Ser Leu Tyr
```

THERMOCOCCUS ONNURINEUS MC02 AND METHOD OF HYDROGEN PRODUCTION USING THEREOF

CROSS-REFERENCE TO RELATED APPLICATION AND CLAIM OF PRIORITY

This application claims the benefit of Korean Patent Application No. 10-2013-0137344, filed Nov. 13, 2013, at the Korean Intellectual Property Office, the disclosures of which are incorporated herein in their entirety by reference.

BACKGROUND

1. Field of the Invention

The present invention relates to *Thermococcus onnurineus* MC02 and a method for producing hydrogen using the same.

2. Background Art

Hydrogen energy is in the spotlight as an alternative to fossil energy since it has three times higher heating power per unit weight than fossil energy and no adverse effect such as emission of carbon dioxide, $NO_x$ or $SO_x$ on environment.

There have been several methods to produce hydrogen such as water electrolysis, thermal cracking of natural gas or naphtha, steam reforming, etc. However, the traditional methods have some problems since they use fossil energy again to make high temperature and high pressure conditions for hydrogen production and generate the gas mixture comprising carbon monoxide having harmful environmental effects.

On the other hand, biological hydrogen production method using an organism has more advantages than the traditional methods since it does not need extra energy for high temperature or high pressure and it does not emit carbon monoxide gas. Such biological hydrogen production methods can be classified into two groups, i.e. a method using photosynthetic microorganisms and a method using non-photosynthetic microorganisms (mainly anaerobic microorganisms).

However, the biological hydrogen production method also have some technical problems since proper techniques for culturing high concentration of photosynthetic microorganisms requiring light as energy source have not been developed yet and the traditional photosynthetic microorganisms show severe substrate inhibition when the concentration of the substrate is high. Also, they can retain the hydrogen production potential only if the light source exists.

The inventors of the present invention discovered rchA gene located in front of the codh-mch-mnh3 cluster and confirmed that a promoter inducing the expressions of rchA gene and codh-mch-mnh3 cluster can increase hydrogen production from carbon monoxide.

SUMMARY

According to an aspect of the present invention, a mutant strain belonged to the genus *Thermococcus* having increased expression of rchA gene as compared to its wild strain is provided.

According to an aspect of the present invention, the mutant strain may have increased replication, transcription and/or translation rate of the gene, stability of a protein expressed by the gene, or combination thereof, as compared to its wild strain.

According to an aspect of the present invention, the mutant strain has a promoter selected from the group consisting of glucose dehydrogenase (gdh) promoter, sigma 70 promoter, pL; Plac; Ptrp; Ptac (Ptrp-lac hybrid promoter) of bacteriophage λ, isopropyl-beta-D44 thiogalactopyranoside (IPTG)-inducible promoter, tetracycline-inducible promoter, arabinose-inducible promoter, xylose-inducible promoter, tryptophan promoter, lac promoter, alcohol-inducible promoter and heat-inducible promoter.

According to an aspect of the present invention, the strain is *Thermococcus onnurineus* MC02 strain, which was deposited under accession number of KCTC12511BP.

According to an aspect of the present invention, a method for producing hydrogen, the method includes preparing a mutant strain belonged to the genus *Thermococcus* having increased expression of rchA gene as compared to its wild strain, and culturing the mutant strain to produce hydrogen.

According to an aspect of the present invention, the culture condition of the strain for hydrogen production comprises a temperature in the range of 60 to 90° C.

According to an aspect of the present invention, a culture condition of the strain for hydrogen production comprises providing the strain with carbon monoxide at a pressure in the range of 1 to 3 atm.

According to an aspect of the present invention, the carbon monoxide is provided in a form of synthetic gas or by-product gas of steel industry.

DETAILED DESCRIPTION

Hereinafter, the present invention will be described in further detail with reference to examples. However, these examples are for illustrative purposes only and it is to be understood by those with common knowledge in the technical field the present invention is part of, that these examples are not to be construed to limit the scope of the present invention.

An embodiment of the present invention provides *Thermococcus onnurineus* MC02 strain.

The developed microorganism, *Thermococcus onnurineus* MC02, was duly deposited with Korean Collection for Type Cultures (KCTC) (having the address of Biological Resource Center (BRC), Korea Research Institute of Bioscience and Biotechnology (KRIBB), 52 Eoeun-dong, Yuseong-gu, Daejeon 305-333, Republic of Korea) under the Access number of KCTC 12511BP on Oct. 31, 2013. The deposit has been made under the terms of the Budapest Treaty and all restrictions imposed by the depositor on the availability to the public of the biological material will be irrevocably removed upon the granting of a patent.

The strain has increased hydrogen production ability, wherein the expression of rchA gene of the strain increases.

The increased expression of the rchA gene may be resulted from the increased replication, transcription or translation rate of the gene, stability of the protein expressed by the gene, or combination thereof.

A powerful promoter may increase the transcription rate of rchA gene. For example, the promoter comprises glucose dehydrogenase (gdh) promoter, sigma 70 promoter, pL; Plac; Ptrp; Ptac (Ptrp-lac hybrid promoter) of bacteriophage λ, isopropyl-beta-D44 thiogalactopyranoside (IPTG)-inducible promoter, tetracycline-inducible promoter, arabinose-inducible promoter, xylose-inducible promoter, tryptophan promoter, lac promoter, alcohol-inducible promoter or heat-inducible promoter.

Another embodiment of the present invention provides a method for producing the strain belonged to the genus *Thermococcus* having increased hydrogen production ability including preparing a mutant strain increasing the expression of rchA gene of the strain. The increase of the expression of rchA gene may include increasing the replication, transcription or translation rate of the gene, stability of the protein expressed by the gene, or combination thereof.

According to an embodiment of the present invention, the increasing the transcription rate of rchA gene may include using a powerful promoter. For example, the promoter comprises glucose dehydrogenase (gdh) promoter, sigma 70 promoter, pL; Plac; Ptrp; Ptac (Ptrp-lac hybrid promoter) of bacteriophage λ, isopropyl-beta-D44 thiogalactopyranoside (IPTG)-inducible promoter, tetracycline-inducible promoter, arabinose-inducible promoter, xylose-inducible promoter, tryptophan promoter, lac promoter, alcohol-inducible promoter or heat-inducible promoter.

In another embodiment of the present invention, a method for hydrogen production includes using the *Thermococcus onnurineus* MC02 strain.

For example, the culture conditions of the strain for hydrogen production include the temperature in the range of 60 to 90° C. and the pressure in the range of 1 to 3 atm under an atmospheric CO (carbon monoxide) environment. In one embodiment, the CO can be provided in a form of synthetic gas or by-product gas of steel industry.

Example 1

Construction of Mutant Strains

Figure 1:
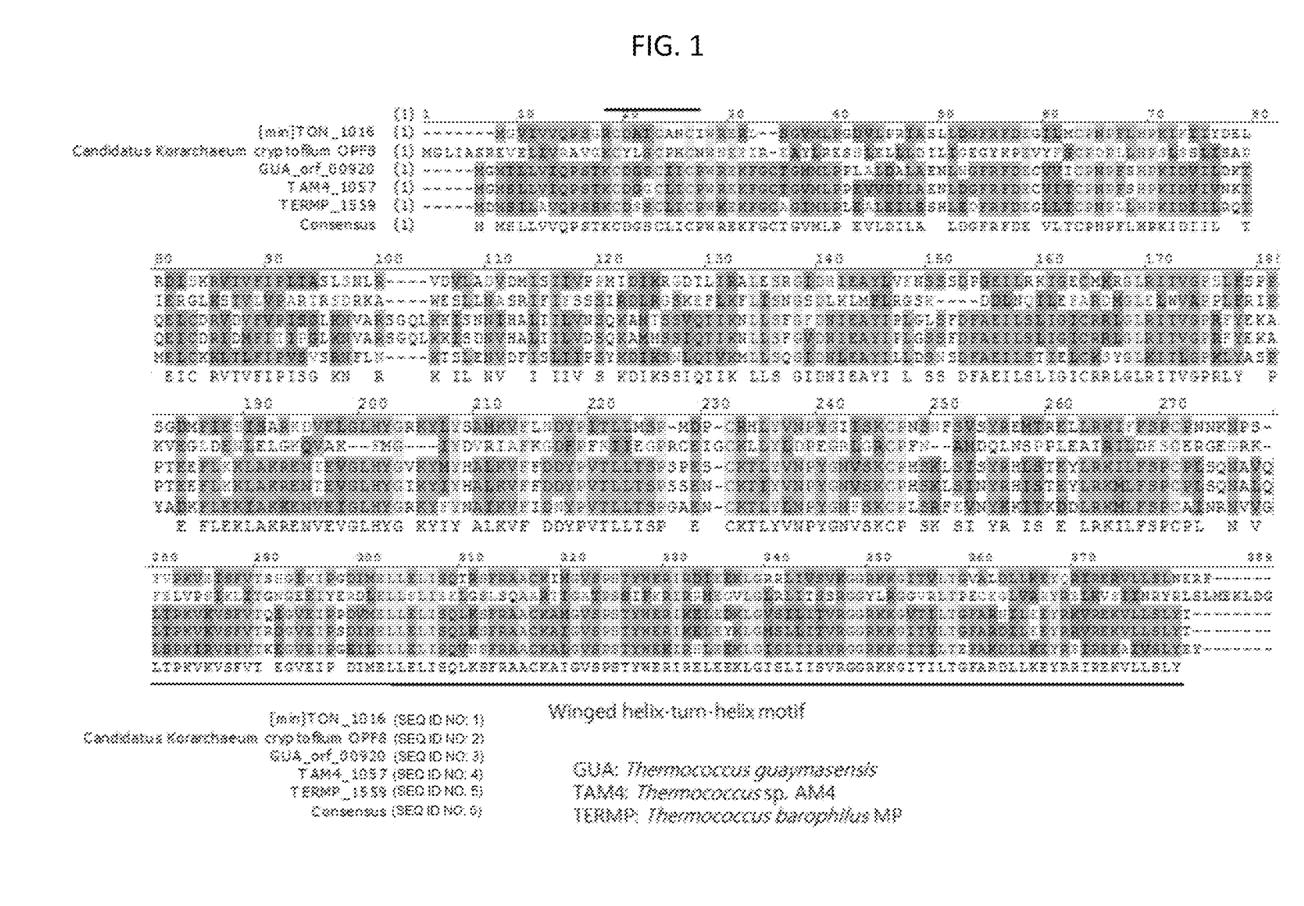
FIG. 1 illustrates sequence alignment of TON_1016.

The rchA gene (TON_1016 and TON_1016-1) was found commonly in front of codh-mch-mnh3 cluster in the strains grown in carbon monoxide conditions such as *Thermococcus onnurineus* NA1, *Thermococcus* sp. AM4, or *Thermococcus* sp. MP., etc. According to the sequence alignment data of rchA protein derived from the strains, it was estimated that the protein may be a regulator binding to DNA by the change of carbon monoxide concentration since it has Fe-S motif at the N-terminal and winged helix-turn-helix motif at the C-terminal (FIG. 1).

Figure 2A:
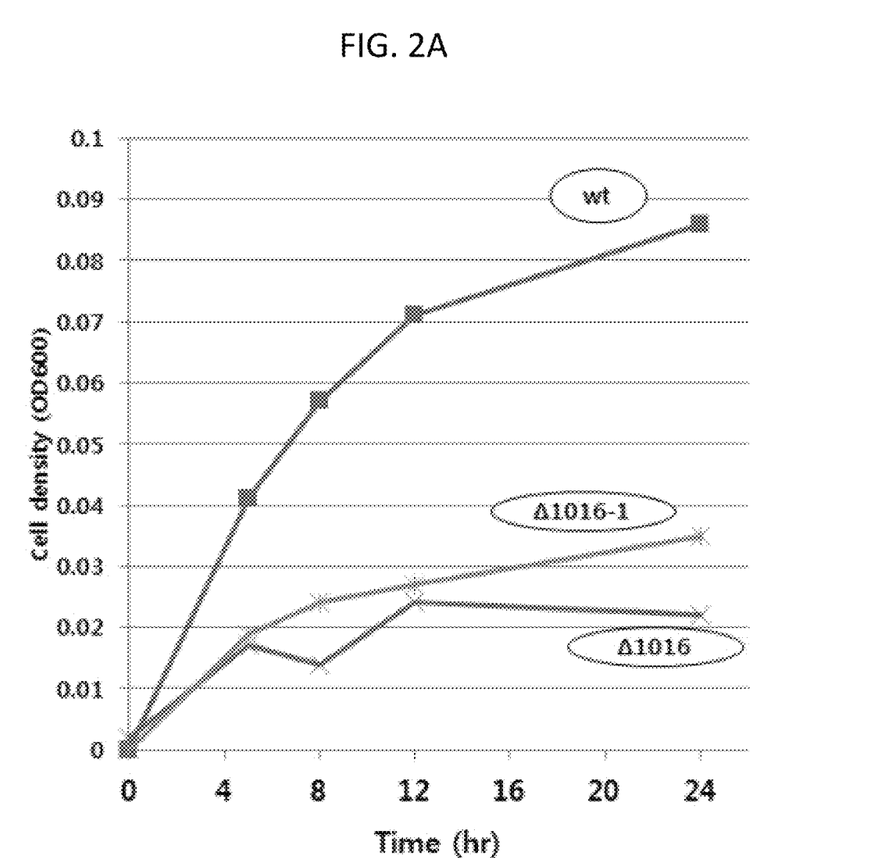
FIGS. 2A and 2B illustrate cell growth (FIG. 2A) and hydrogen production rates (FIG. 2B) of TON_1016 and TON_1016-1 gene knockout mutant compared with wild-type.
Figure 2B:
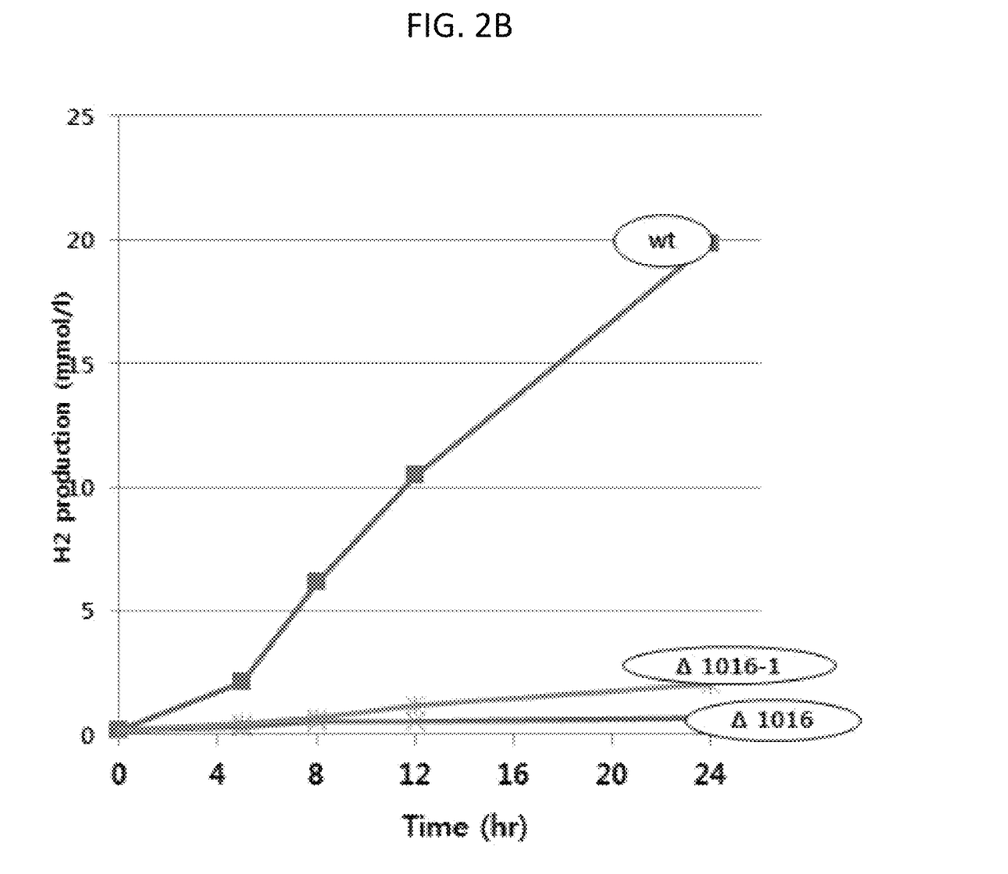

Based on the estimations, we constructed rchA gene (TON_1016 and TON_1016-1) knockout mutant, and confirmed that rchA gene (TON_1016, TON_1016-1) is essential for growth and hydrogen production of the strains using carbon monoxide from the growth and hydrogen production rates of the mutant in carbon monoxide conditions compared with the wild-type (FIGS. 2A and 2B).

Figure 3:
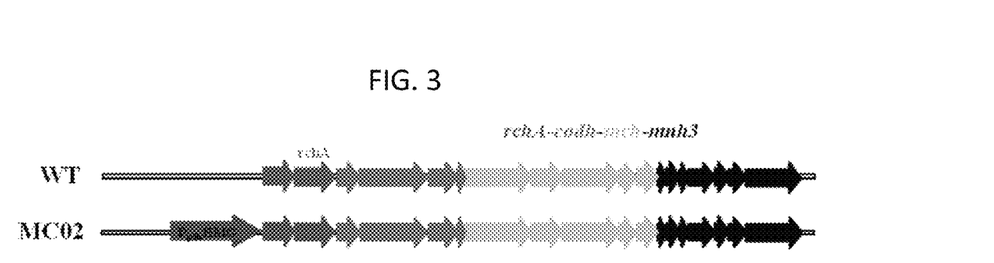
FIG. 3 illustrates a construction of a promoter insertion mutant.

Thus, based on the results, we decided to obtain the strains demonstrating high activity, overexpressing codh-mch-mnh3 cluster under the carbon monoxide condition by overexpression of the regulator gene, rchA and having increased ability to regulate expression of the genes which may be related to carbon monoxide toxicity. We attempted to construct the strain (MC02) by inserting a powerful promoter upstream of rchA gene (FIG. 3).

Example 2

Hydrogen Production Ability of Mutant Strains

To evaluate cell growth and hydrogen production ability of the strain demonstrating high activity (MC02), we performed comparative experiments using MM1 culture medium with 10 g/l yeast at working volume 2 in 3 L continuous stirred-tank reactor (CSTR) equipped with mesh 5 μm spargera, under the conditions of 80° C. and 300 rpm, with a supply of 0.2 vvm of 100% carbon monoxide gas.

Figure 4A:
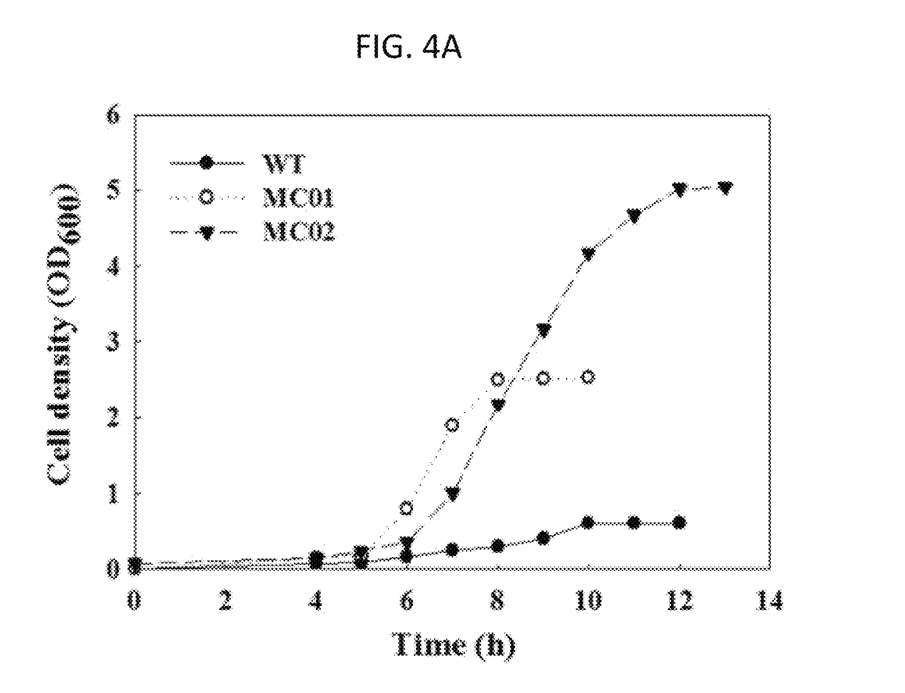
FIGS. 4A and 4B illustrate cell growth (FIG. 4A) and hydrogen production rates (FIG. 4B) of MC02 strains demonstrating high activity.
Figure 4B:
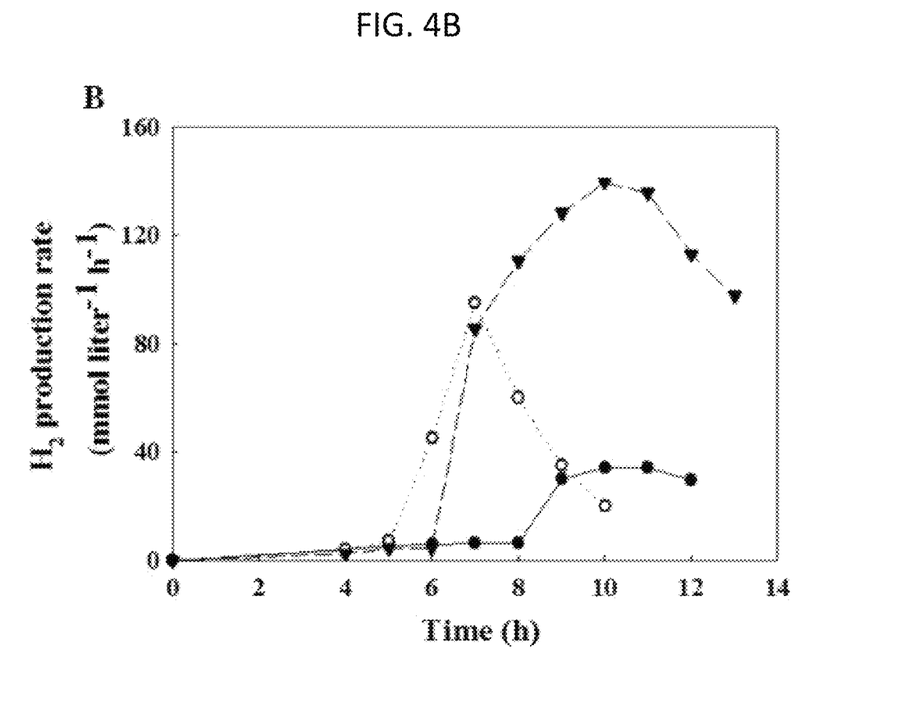
Figure 5A:
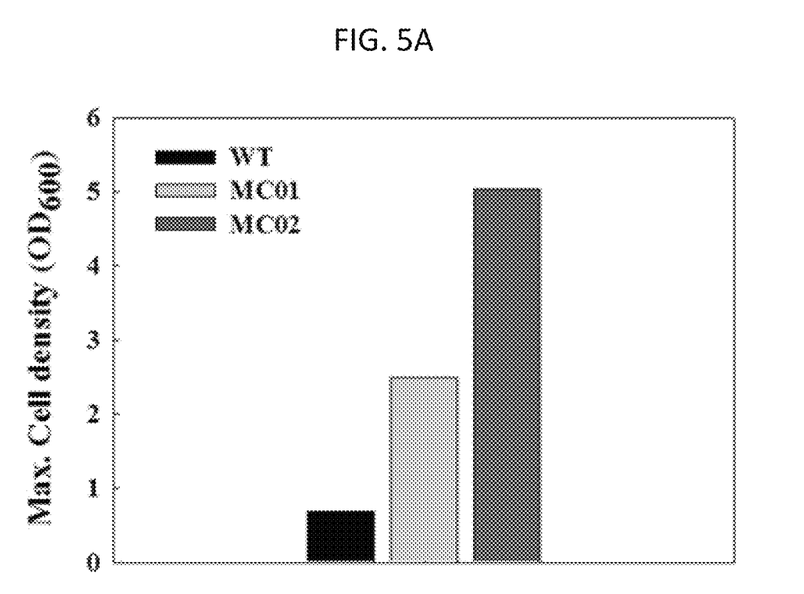
FIGS. 5A and 5B illustrate maximum cell growth (FIG. 5A) and maximum hydrogen production rate (FIG. 5B) of MC01 and MC02 strains demonstrating high activity compared with wild-type (NA1).
Figure 5B:
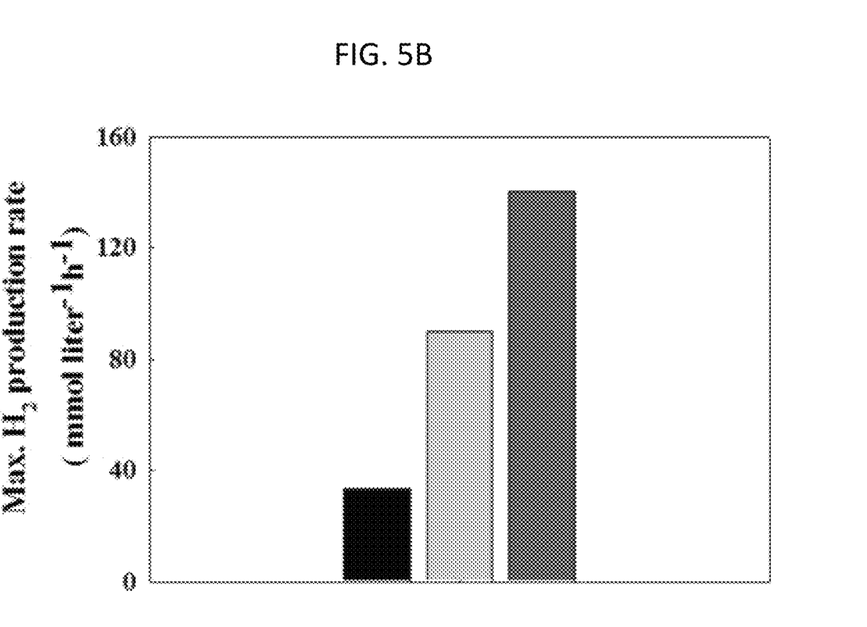

According to the maximum cell concentration results, OD(600 nm) of MC02 strain was 5 after 12 hr of culture and OD(600 nm) of MC01 strain was 2.5 after 8 hr of culture and OD(600 nm) of wild-type NA1 strain was 0.5 after 10 hr of culture, when 0.2 vvm of carbon monoxide had been supplied (FIG. 4A). According to the hydrogen production results, the maximum hydrogen production rates of the wild-type, MC01 and MC02 strains were approximately 32 mmol/l/h, 100 mmol/l/h and 140 mmol/l/h, respectively (FIG. 4B). The maximum hydrogen production rate of the MC02 is 4.4 times higher than that of the wild-type and 1.4 times higher than that of the MC01 which has been reported as a strain having high activity (FIGS. 5A and 5B), indicating that the MC02 has the best hydrogen production ability among the reported strains.

Example 3

Avoidance of Carbon Monoxide Poisoning in Mutant Strains

It is important to facilitate the use of substrate easily by increasing mass transfer rate of carbon monoxide, to use carbon monoxide as a substrate. However, as the mass transfer rate of carbon monoxide gets higher, the activity of metal containing enzyme or an enzyme using CO such as CODH in cell may be inhibited, resulting in the inhibition of cell growth and hydrogen production through carbon monoxide poisoning.

However, the MC02 strain overexpressing the regulator, rchA may avoid carbon monoxide poisoning by regulating the expressions of regulons other than codh cluster. Thus, we performed experiments to examine the ability of the strain to avoid carbon monoxide poisoning by increasing the supply of carbon monoxide from 0.2 vvm up to 0.3 or 0.4 vvm. To evaluate cell growth and hydrogen production ability of the strain demonstrating high activity (MC02), we performed comparative experiments using MM1 culture medium with 10 g/l yeast at working volume 2 in 3 L continuous stirred-tank reactor (CSTR) equipped with mesh spargera, at 80 to 300 rpm, with a supply of 0.2, 0.3 and 0.4 vvm of 100% carbon monoxide gas.

Figure 6A:
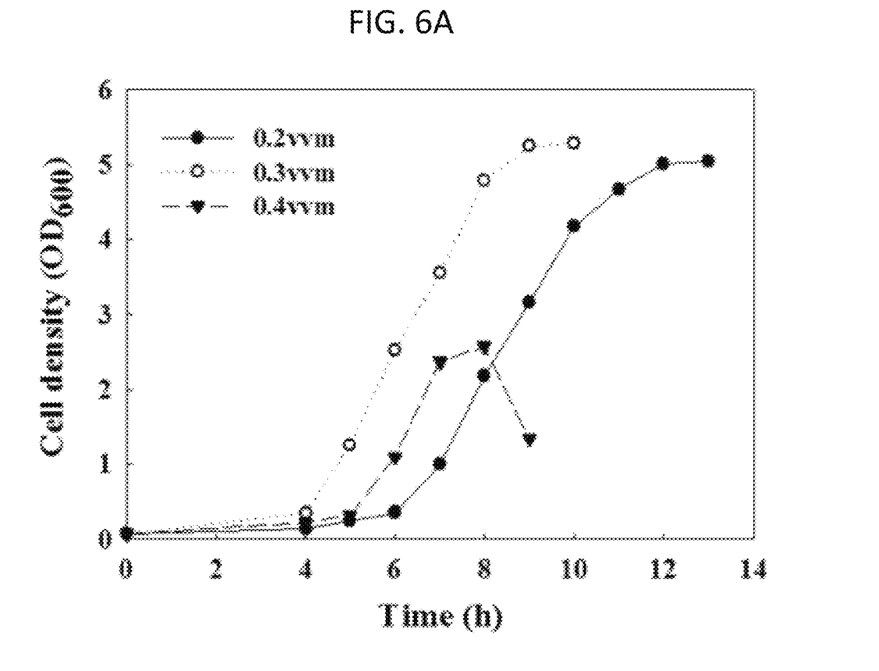
FIGS. 6A and 6B illustrate cell growth (FIG. 6A) and hydrogen production rates (FIG. 6B) of MC02 strains demonstrating high activity by carbon monoxide supply.
Figure 6B:
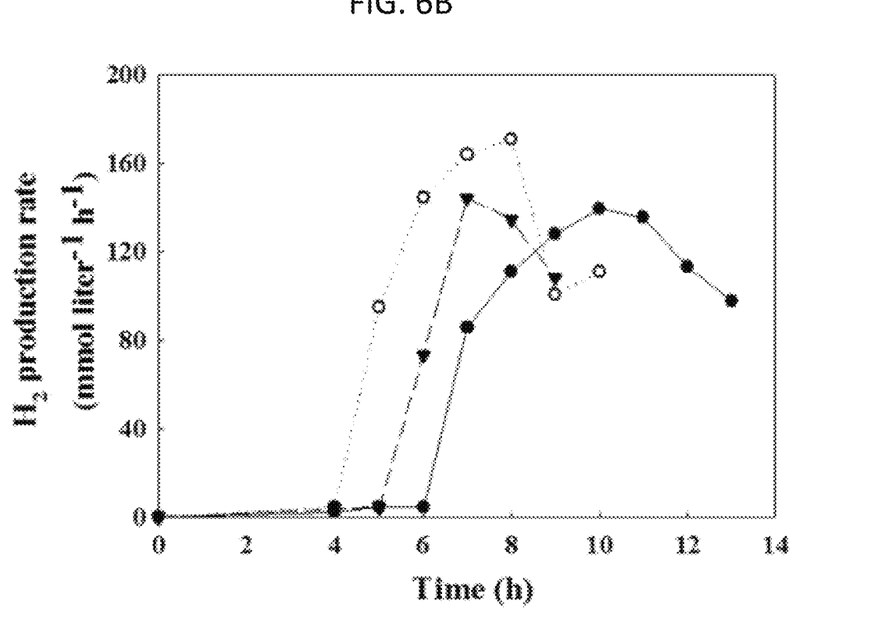
Figure 7A:
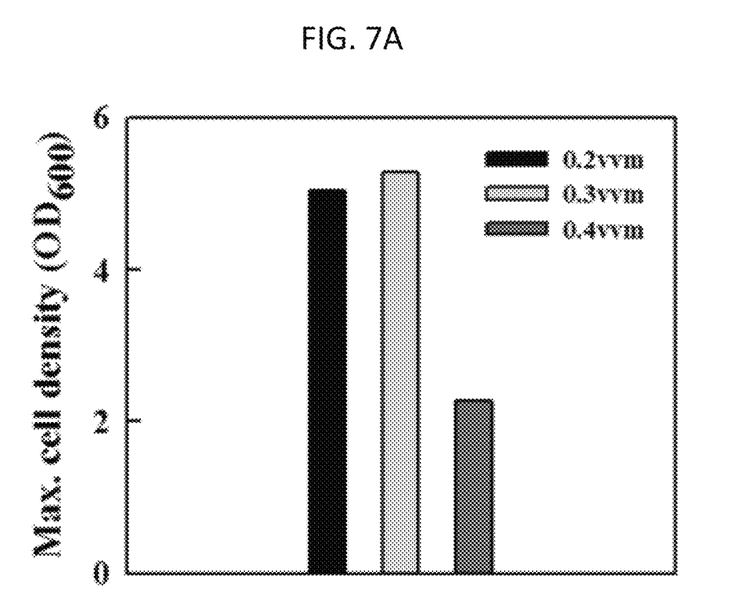
FIGS. 7A and 7B illustrate maximum cell growth (FIG. 7A) and maximum hydrogen production rate (FIG. 7B) of MC02 strains demonstrating high activity by carbon monoxide supply.
Figure 7B:
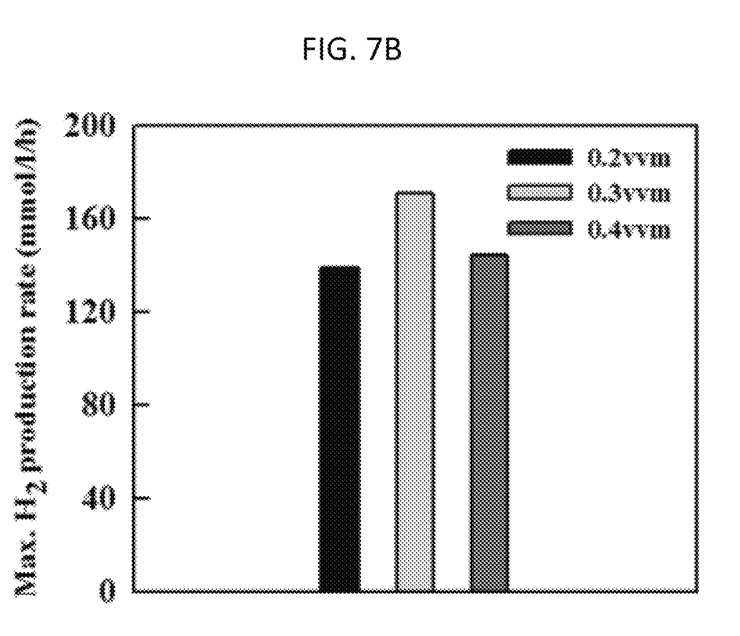

According to the maximum cell concentration results, OD(600 nm) of MC02 strain was 5 after 10 hr of culture with a supply of 0.2 vvm carbon monoxide, 5.3 after 10 hr of culture with a supply of 0.3 vvm carbon monoxide, and 2.5 after 8 hr of culture with a supply of 0.4 vvm carbon monoxide (FIG. 6A). According to the hydrogen production results, the maximum hydrogen production rates were about 140 mmol/l/h with 0.2 vvm carbon monoxide, 170 mmol/l/h with 0.3 vvm carbon monoxide, and 140 mmol/l/h with 0.4 vvm carbon monoxide (FIG. 6B). The supply of 0.2 or 0.3 vvm carbon monoxide did not affect the maximum cell concentration (FIG. 7A) and hydrogen production (FIG. 7B) of the MC02 unlike the wild-type, whereas the supply of 0.4 vvm carbon monoxide affected both the maximum cell concentration and hydrogen production of the MC02.

In conclusion, the selected strain MC02 can show the maximum cell concentration and hydrogen production up to 0.3 vvm carbon monoxide condition unlike wild-type.

*Thermococcus onnurineus* MC02 strain according to an embodiment of the present invention shows greater growth rate and hydrogen production ability in the condition of high concentration of carbon monoxide than wild-type strain. And the method for hydrogen production according to the present invention can produce hydrogen efficiently with lower cost and use synthetic gas or by-product gas of steel industry.

What is claimed is:

1. A strain of *Thermococcus onnurineus* MC02, which was deposited under accession number of KCTC12511BP.

2. A method for producing hydrogen, the method comprising:
preparing the strain of claim 1; and
culturing the strain to produce hydrogen.

3. The method of claim 2, wherein a culture condition of the strain for hydrogen production comprises a temperature in the range of 60 to 90° C.

4. The method of claim 2, wherein culture condition of the strain for hydrogen production comprises providing the strain with carbon monoxide at a pressure in the range of 1 to 3 atm.

5. The method of claim 4, wherein the carbon monoxide is provided in a form of synthetic gas or by-product gas of steel industry.

* * * * *